(12) United States Patent
Davis et al.

(10) Patent No.: US 8,067,011 B2
(45) Date of Patent: *Nov. 29, 2011

(54) COMPOSITIONS AND METHODS FOR TREATING B-CELL MALIGNANCIES

(75) Inventors: Claude Geoffrey Davis, San Mateo, CA (US); Miguel A. de los Rios, Ventura, CA (US); Kenneth J. Oh, Santa Barbara, CA (US); Timothy L. Bullock, Goleta, CA (US); Patrick T. Johnson, Santa Barbara, CA (US); Jacek Ostrowski, Goleta, CA (US)

(73) Assignee: Chimeros, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/697,945

(22) Filed: Apr. 9, 2007

(65) Prior Publication Data

US 2007/0269370 A1 Nov. 22, 2007

Related U.S. Application Data

(60) Provisional application No. 60/790,321, filed on Apr. 7, 2006.

(51) Int. Cl.
*A61K 39/29* (2006.01)
*A61K 39/385* (2006.01)
*C07K 14/02* (2006.01)

(52) U.S. Cl. ............ 424/189.1; 424/194.1; 424/196.11; 424/201.1; 424/227.1; 424/192.1; 530/350; 530/402; 977/795; 977/797; 977/798; 977/800; 977/801; 977/802

(58) Field of Classification Search .................. None
See application file for complete search history.

(56) References Cited

U.S. PATENT DOCUMENTS

| | | | |
|---|---|---|---|
| 5,133,961 A | 7/1992 | Ellis et al. | |
| 5,420,026 A | 5/1995 | Payne | |
| 5,439,686 A | 8/1995 | Desai et al. | |
| 5,498,421 A | 3/1996 | Grinstaff et al. | |
| 5,670,630 A | 9/1997 | Thill | |
| 5,714,316 A | 2/1998 | Weiner et al. | |
| 5,858,726 A | 1/1999 | Payne | |
| 5,863,541 A | 1/1999 | Samulski et al. | 424/192.1 |
| 5,980,901 A | 11/1999 | Shih et al. | |
| 6,046,173 A | 4/2000 | Forstova et al. | 514/44 |
| 6,063,370 A | 5/2000 | Dadey | |
| 6,096,331 A | 8/2000 | Desai et al. | |
| 6,204,059 B1 | 3/2001 | Samulski et al. | 435/456 |
| 6,231,864 B1 * | 5/2001 | Birkett | 424/189.1 |
| 6,387,662 B1 | 5/2002 | Liang et al. | |
| 6,420,160 B1 | 7/2002 | Bloch | 435/239 |
| 6,506,405 B1 | 1/2003 | Desai et al. | |
| 6,506,559 B1 | 1/2003 | Fire et al. | |
| 6,537,579 B1 | 3/2003 | Desai et al. | |
| 6,573,009 B1 | 6/2003 | Noda et al. | |
| 6,602,706 B1 | 8/2003 | Fallaux et al. | |
| 6,602,932 B2 | 8/2003 | Feldheim et al. | |
| 6,616,944 B2 | 9/2003 | Kissel et al. | |
| 6,620,617 B2 | 9/2003 | Mathiowitz et al. | |
| 6,627,202 B2 | 9/2003 | Murray et al. | |
| 6,696,038 B1 | 2/2004 | Mahato et al. | |
| 6,710,173 B1 | 3/2004 | Binley et al. | |
| 6,749,868 B1 | 6/2004 | Desai et al. | |
| 6,753,006 B1 | 6/2004 | Desai et al. | |
| 6,984,386 B2 | 1/2006 | Douglas et al. | 424/204.1 |
| 7,056,704 B2 | 6/2006 | Tuschl et al. | |
| 7,078,194 B2 | 7/2006 | Withers et al. | |
| 7,101,995 B2 | 9/2006 | Lewis et al. | 536/55 |
| 7,282,199 B2 | 10/2007 | Gao et al. | |
| 7,332,321 B2 | 2/2008 | Belcher et al. | |
| 7,332,337 B2 | 2/2008 | van Es et al. | |
| 7,344,872 B2 | 3/2008 | Gao et al. | |
| 7,422,902 B1 | 9/2008 | Wheeler et al. | |
| 2004/0005338 A1 | 1/2004 | Bachmann et al. | |
| 2004/0247660 A1 | 12/2004 | Singh | |
| 2005/0004002 A1 | 1/2005 | Desai et al. | |
| 2005/0089526 A1 | 4/2005 | Moore et al. | |
| 2006/0292118 A1 | 12/2006 | Kuroda et al. | 424/93.2 |
| 2006/0292174 A1 | 12/2006 | de los Rios et al. | |
| 2007/0248573 A1 | 10/2007 | Sturino | |
| 2007/0249554 A1 | 10/2007 | Tuszynski | |
| 2007/0258889 A1 | 11/2007 | Douglas et al. | |
| 2007/0269370 A1 | 11/2007 | Davis et al. | |
| 2007/0280962 A1 | 12/2007 | Murray | |
| 2008/0050343 A1 | 2/2008 | Wilson et al. | |
| 2008/0050345 A1 | 2/2008 | Wilson et al. | |
| 2008/0069802 A1 | 3/2008 | Davis et al. | |
| 2008/0075737 A1 | 3/2008 | Gao et al. | |
| 2008/0075740 A1 | 3/2008 | Gao et al. | |
| 2008/0090281 A1 | 4/2008 | Wilson et al. | |

(Continued)

FOREIGN PATENT DOCUMENTS

EP 863987 9/1998

(Continued)

OTHER PUBLICATIONS

Larsen SR, Rasko JE. "Lymphoproliferative disorders: prospects for gene therapy." Pathology. Dec. 2005;37(6):523-33.*
de Kruif J, Storm G, van Bloois L, Logtenberg T. "Biosynthetically lipid-modified human scFv fragments from phage display libraries as targeting molecules for immunoliposomes." FEBS Lett. Dec. 16, 1996;399(3):232-6.*
Mansfield E, Amlot P, Pastan I, FitzGerald DJ. "Recombinant RFB4 immunotoxins exhibit potent cytotoxic activity for CD22-bearing cells and tumors." Blood. Sep. 1, 1997;90(5):2020-6.*
Moreira J. et al. "Use of the post-insertion technique to insert peptide ligands into pre-formed Stealth liposomes with retention of binding activity and cytotoxicity" Pharmaceutical Research 19(3):265-269, 2002.*
Scott MD, et al. "Chemical camouflage of antigenic determinants: stealth erythrocytes" Proc Natl Acad Sci U S A. Jul. 8, 1997;94(14):7566-71.*
Xia H, et al. "siRNA-mediated gene silencing in vitro and in vivo". Nat Biotechnol 2002; 20: 1006-10.*
Rubinson DA, et al. A lentivirus-based system to functionally silence genes in primary mammalian cells, stem cells and transgenic mice by RNA interference. Nat Genet 2003; 33:401-6.*

(Continued)

*Primary Examiner* — Bo Peng
(74) *Attorney, Agent, or Firm* — Goodwin Procter LLP

(57) ABSTRACT

The present invention provides a targeted multi-layered drug delivery system for the delivery of cytotoxic agents to B-cells.

28 Claims, 7 Drawing Sheets

U.S. PATENT DOCUMENTS

| | | | |
|---|---|---|---|
| 2008/0125385 | A1 | 5/2008 | Hajjar et al. |
| 2008/0131928 | A1 | 6/2008 | Handa et al. |
| 2009/0226525 | A1 | 9/2009 | de los Rios et al. |

FOREIGN PATENT DOCUMENTS

| | | | |
|---|---|---|---|
| EP | 920514 | | 6/1999 |
| EP | 1204761 | | 5/2002 |
| EP | 1219705 | | 7/2002 |
| EP | 1 447 079 | A1 | 8/2004 |
| EP | 1563834 | | 8/2005 |
| EP | 1845163 | A2 | 10/2007 |
| EP | 1849799 | A1 | 10/2007 |
| EP | 1944043 | A1 | 7/2008 |
| WO | WO 95/32706 | | 12/1995 |
| WO | WO-99/40214 | | 8/1999 |
| WO | WO 00/09158 | | 2/2000 |
| WO | WO-01/02551 | | 1/2001 |
| WO | WO 01/12235 | A2 | 2/2001 |
| WO | WO 02/44204 | | 6/2002 |
| WO | WO-2004/047812 | | 6/2004 |
| WO | WO-2006/033679 | | 3/2006 |
| WO | WO-2006/066048 | | 6/2006 |
| WO | WO-2007/126764 | | 11/2007 |
| WO | WO-2007/136263 | | 11/2007 |
| WO | WO-2008/008881 | | 1/2008 |
| WO | WO-2008/010864 | A2 | 1/2008 |
| WO | WO-2008/021908 | | 2/2008 |
| WO | WO-2008/024427 | | 2/2008 |
| WO | WO-2008/027084 | A2 | 3/2008 |
| WO | WO-2008/037504 | | 4/2008 |
| WO | WO-2008/048288 | A2 | 4/2008 |
| WO | WO-2008/051101 | | 5/2008 |
| WO | WO-2008/054826 | | 5/2008 |
| WO | WO-2008/124165 | | 10/2008 |

OTHER PUBLICATIONS

Fasbender et al., "Complexes of Adenovirus with Polycationic Polymers and Cationic Lipids Increase the Efficiency of Gene Transfer in Vitro and Vivo", *J. Biol. Chem.*, 272(10): 6479-6489 (1997).
Boisgerault et al. "Virus-like particles: a new family of delivery systems" Expert Rev. Vaccines 1(1):101-9, 2002.
Bottcher et al. "Determination of the fold of the core protein of hepatitis B virus by electron cryomicroscopy" Nature 386:88-91, 1997.
Brumfield et al. "Heterologous expression of the modified coat protein of Cowpea chlorotic mottle bromovirus results in the assembly of protein cages with altered architecture and function" J. gen Virol 85:1049-1053, 2004.
Crommelin et al. "Nanotechnological approaches for the delivery of macromolecules" J Controlled Release 87:81-88, 2003.
Crowther et al. "Three-dimensional structure of hepatitis B virus core particles determined by electronic cryomicroscopy" Cell 77:943-50, 1994.
DeNardo et al. "Efficacy and Toxicity of 67Cu-2IT-BAT-Lym-1 Radio-immunoconjugate in Mice Implanted with Human Burkitt's Lymphoma (Raji)" Cln. Cancer Res., 3:71-79 (1997).
Fernandez et al. "Activated protein C Correlates Inversely with Thrombin Levels in Resting Healthy Individuals" Am. J. Hematol., 56:29-31 (1997).
Haag "Supramolecular drug-delivery systems based on polymeric core-shell architectures" Angew Chem Int Ed 43:278-282, 2004.
International Search Report for PCT/US07/08938, dated Oct. 7, 2008.
International Search Report for PCT/US08/04585, dated Mar. 17, 2009.
International Search Report for PCT/US05/18456, dated Sep. 13, 2006.
Jenny et al. "A critical review of the methods for cleavage of fusion proteins with thrombin and factor Xa" Prot Express Purif 31:1-11, 2003.
Kayser et al. "Formulation and biopharmaceutical issues in the development of drug delivery systems for antiparasitic drugs" Parasitol Res 90:S63-S270, 2003.
Lamprecht et al. "Biodegradable nanoparticles for targeted drug delivery in treatment of inflammatory bowel disease" J Pharmacol Exp Ther 299:775-81, 2002.
Liu et al. "Nanostructured materials designed for cell binding transduction" Biomacromolecules 2:362-368, 2001.
Lundstrom et al. "Breakthrough in cancer therapy: encapsulation of drugs and viruses" Curr Drug Disc: Nov. 2002, pp. 19-23.
Maeda "The enhanced permeability and retention (EPR) effect in tumor vasculature: the key role of tumor-selective macromolecular drug targeting" Adv Enzyme Regul 41:189-207, 2001.
Managit et al. "Targeted and sustained drug delivery using PEGylated galatosylated liposomes" Int J Pharmaceutics 266:77-84, 2003.
Martin et al. "Immunospecific targeting of lipsomes to cells: a novel and efficient method for covalent attachment of Fab' fragments via disulfide bonds" Biochemistry 20:4229-38, 1981.
Moghimi et al. "Long-circulated and target-specific nanoparticles: theory to practice" Pharmacol Rev 53:283-318, 2001.
Monsky et al. "Augmentation of transvascular transport of macromolecules and nanoparticles in tumors using vascular endothelial growth factor" Cancer Res. 59:4129-35, 1999.
Paddison et al. "Stable Expression of Gene Suppression by RNAi in mammalian cells" PNAS, vol. 99, No. 3, pp. 1443-1448, 2002.
Panyam et al. "Fluorescence and electron microscopy probes for cellular tissue uptake of poly(D,L-lactide-co-glycolide-nanoparticles" Int J. Pharm 262:1-11, 2003.
Panyam et al. "Biodegradable nanoparticles for drug and gene delivery to cells and tissue" Adv Drug Del Rev 55:329-47, 2003.
Roco et al. "Societal Implications of Nanoscience and Technology" National Science Foundation Report, 2001.
Rosenthal et al. "Viral workhorses" Scientific American, Sep. 2, 2002.
Sahoo et al. "Nanotech approaches to drug delivery and imaging" Drug Disc Today 8:1112-1120, 2003.
Sahoo et al. "Pegylated zinc protoporphyrin: a water-soluble heme oxygenase inhibitor with tumor targeting capacity" Bioconjugate Chem 13:1031-8, 2002.
Schmidt et al. "Binding of external ligands onto an engineered virus capsid" Protein Eng 14:769-774, 2001.
Schmidt et al. "Protein and peptide delivery via engineered polymavirus-like particles" FASEB J 15:1646-1648, 2001.
Sinha et al. "Biodegradable miscrospheres for protein delivery" J Controlled Rel 90:261-280, 2003.
Wynne et al. "The crystal structure of the human hepatitis B virus capsid" Molecular Cell 3:771-80, 1999.
Stevens "The cost and value of three-dimensional protein structure" Drug Disc. World 4, 4:35-48 (2003).
Zlotnick "Are weak protein-protein interactions the general rule in capsid assembly?" Virology, 315:269-274 (2003).
Yamada et al. "Nanoparticles for the Delivery of Genes and Drugs to Human Hepatocytes" Nature Biotechnology, vol. 21, No. 89, 2003, pp. 885-890.
Hashida et al. "Fusion of HIV-1 Tat protein transduction domain to poly-lisine as a new DNA delivery tool" British J. of Cancer, Nature Publ. Group., London, GB, vol. 90, No. 6, pp. 1252-1258, 2004.
Mansfield et al. "Recombinant RFB4 Immunotoxins Exhibit Potent Cytotoxic Activity for CD22-Bearing Cells and Tumors" Blood, Sep. 1, 1997;90(5):2020-6.
Perales et al. "An evaluation of receptor-mediated gene transfer using synthetic DNA-ligand complexes" European J of Biochemistry, Berlin, vol. 226, No. 2, pp. 255-266, 1994.
Wagner et aL "Transferrin-polycation-DNA complexes: The effect of polycations on the structure of the complex and DNA delivery to cells" Proceedings of the National Academy of Science of USA, Nat'l Acad. of Sci., vol. 88, No. 10, pp. 4255-4259, 1991.

* cited by examiner

SEQUENCE LISTING

<160> NUMBER OF SEQ ID NOS: 2

<210> SEQ ID NO 1
<211> LENGTH: 183
<212> TYPE: PRT
<213> ORGANISM: Hepatitis B virus

<400> SEQUENCE: 1

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Pro His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 2
<211> LENGTH: 23
<212> TYPE: PRT
<213> ORGANISM: Hepatitis B virus

<400> SEQUENCE: 2

```
Cys Ala Arg Gly Ala Arg Gly Ala Arg Gly Ala Arg Gly Ile Leu Gly
1               5                   10                  15

Val Phe Ile Leu Leu Tyr Met
            20
```

COMPOSITIONS AND METHODS FOR TREATING B-CELL MALIGNANCIES

RELATED APPLICATIONS

This application claims the benefit of U.S. Ser. No. 60/790,321, filed Apr. 7, 2006 the content of which is incorporated herein by reference in its entirety.

FIELD OF THE INVENTION

The invention relates generally to compositions and methods for treating cancer and autoimmune disease.

BACKGROUND OF THE INVENTION

Despite years of research into the development of new methods of treatment, cancers of the lymphoid system, lymphomas and certain leukemias, remain quite common. For example, more than 63,000 people in the United States are diagnosed with lymphoma each year, including more than 56,000 cases of non-Hodgkin's Lymphoma (NHL). In addition, there are about 10,000 cases of chronic lymphocytic leukemia (CLL) and 4000 cases of acute lymphocytic leukemia (ALL) diagnosed in the United States each year. Approximately 85% of the NHL, CLL, and ALL cases as a group are derived from B lymphocytes. The prognosis for those affected by these diseases is often poor, as the survival rates for lymphoma patients remain low. New methods for treating these diseases are needed.

While traditional treatments for lymphoma typically depend on the type of lymphoma as well as the medical history of the patient, first-line treatment for many lymphomas typically includes chemotherapy. Such chemotherapy will often entail the administration of a "cocktail" of compounds, e.g., the formulation CHOP, which includes cyclophosphamide, doxorubicin, vincristine, and prednisone. In addition, certain first-line cancer treatments also include other forms of cancer therapy, such as radiation or antibody therapy. In many cases, patients respond initially to such first-line treatments, but subsequently suffer a relapse, i.e., a tumor reappears or resumes growing. Following one such relapse, patients are often treated with further chemotherapy, e.g., with CHOP or with other formulations, or, in some cases, the patients are treated with other procedures such as bone marrow transplantation.

Antibody therapies take advantage of the fact that lymphoid cells express cell surface markers that are restricted to specific lymphoid cell types. For example, the antibody most frequently used for the treatment of B cell-derived lymphomas and leukemias, Rituxan, specifically binds to CD20, which is restricted in its expression to B lymphocytes. Rituxan is used as a naked antibody and effectively depletes both normal and cancerous B cells. Rituxan has been approved for the treatment of patients with relapsed or refractory, low-grade or follicular, CD20-positive, B-cell non-Hodgkin's lymphoma (NHL), in which scenario it has shown a response rate of about 50% and a median duration of response, defined as progression free survival, of about 1 year. Rituxan has also been approved for the first-line treatment of diffuse large B-cell, CD20-positive, non-Hodgkin's lymphoma (DL-BCL-a type of NHL) in combination with CHOP (cyclophosphamide, doxorubicin, vincristine and prednisone) or other anthracycline-based chemotherapy regimens. In this scenario, the addition of Rituxan extends progression free survival over that seen with chemotherapy alone by about 1.5 years. Multiple mechanisms of action are thought to contribute to Rituxan's cytotoxic effect, including antibody dependent cellular cytotoxicity and complement dependent cytotoxicity. The long residence time of CD20 on the cell surface and its resistance to internalization following antibody binding contribute to the ability of Rituxan to focus these natural immune functions on the cancer cell.

The success of Rituxan has spurred multiple drug development programs focused on CD20. Two radiolabelled antibodies specific for CD20, Zevalin and Bexxar, are already on the market. Several companies have new CD20-specific antibodies in clinical development. Antibody mimetics targeting CD20 are also in various stages of development. While future CD20-specific biologics may provide further improvement in response rate and duration of response over those attained with Rituxan, it is nearly certain that there will still be many patients who do not respond at all to CD20-targeted therapy or who will require a different class of drugs following relapse.

CD22 is another surface molecule restricted in its expression to B lymphocytes. CD22 is expressed in 60-80% of B cell malignancies. Naked antibodies and radiolabelled antibodies have shown encouraging results in treating NHL, either as monotherapy or in combination with chemotherapeutics or Rituxan. Further, the fact that CD22, unlike CD20, readily internalizes following antibody binding has opened the door to the development of immunotoxins, antibodies that are conjugated to toxic moieties that are released once inside the target cell. While immunotoxins are often very potent, they frequently cause undesirable toxicities, including death. The toxicities seen with immunotoxins are thought to derive in large part from extracellular release of the toxins.

Mantle cell lymphoma is an example of an aggressive, non-Hodgkins lymphoma. Mantle cell lymphoma is found in lymph nodes, the spleen, bone marrow, blood, and sometimes the gastrointestinal system (lymphomatous polyposis). Mantle cell lymphoma is generally characterized by CD5-positive follicular mantle B cells, a translocation of chromosomes 11 and 14, and an overexpression of the cyclin D1 protein. Like the low-grade lymphomas, mantle cell lymphoma appears incurable with anthracycline-based chemotherapy and occurs in older patients with generally asymptomatic advanced-stage disease. However, the median survival is significantly shorter (3-5 years) than that of other lymphomas; hence this histology is now considered to be an aggressive lymphoma.

Drugs that specifically target B lymphocytes are also candidate therapeutics for the treatment of autoimmune diseases. Most notably, Rituxan has been approved for the treatment of rheumatoid arthritis. Additional anti-CD20 antibodies and antibody mimetics as well as biologics targeting CD22 are also likely to be effective in treating rheumatoid arthritis as well as other autoimmune diseases.

SUMMARY OF THE INVENTION

The invention provides novel therapeutics for the treatment of B-cell malignancies and autoimmune disorders. A B-cell malignancy is for example B-cell lymphoma or leukemia. An autoimmune disorder is for example rheumatoid arthritis, systemic lupus erythematosus, multiple sclerosis, type 1 diabetes, Crohn's disease or ulcerative colitis. The drug delivery system is stable in the extracelluar milieu but rapidly falls apart inside the cell releasing a cytotoxic agent capable of killing the cell. The drug delivery system contains a targeting moiety that allows for the selective targeting of specific cell types to be killed.

The drug delivery system is multi-layered. A first layer is a nanocage that is made by the self assembly of a plurality of viral proteins. The viral protein is a Hepatitis B virus core protein or mutant thereof. During the assembly process the first layer encapsulates the cytotoxic agent. The cytotoxic agent is a toxin, chemotherapeutic agent or radiochemical. The second layer that surrounds the nanocage is a lipid bilayer of a plurality of lipids, e.g., cationic or anionic lipids. A B-cell targeting moiety is anchored in the lipid bi-layer. The B-cell targeting moiety is an anti-CD22 antibody, an anti-CD20 antibody, an anti-CD19 antibody, an anti-immunoglobulin antibody, an anti-FcR-H1 antibody, an anti-CD80 antibody, an anti-CD52 antibody, or a fragment or mimetic thereof. For example, the B-cell targeting moiety is a microprotein. Further, the B cell targeting moiety may be a combination of any of the foregoing.

Also included in the invention is a method of treating or alleviating a sign or symptom of a B-cell malignancy or an autoimmune disorder by administering to a subject, e.g., a mammal such as a human, the drug delivery system according to the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
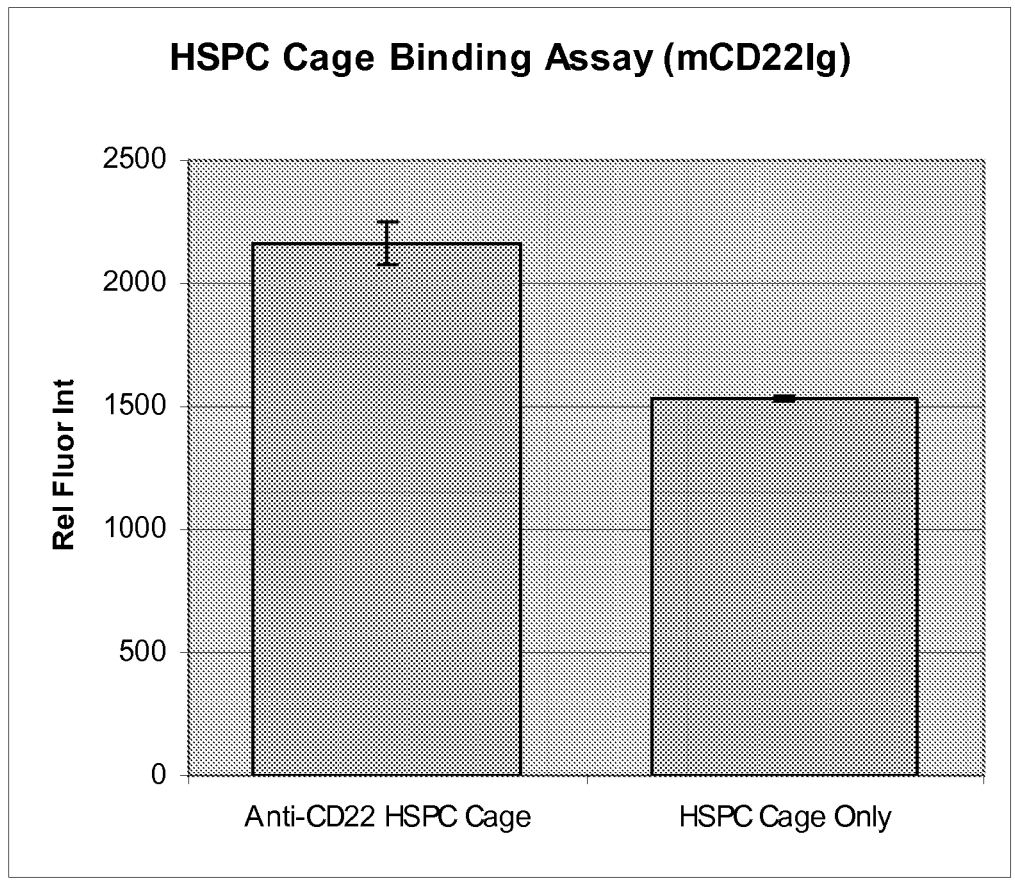
FIG. 1 is a bar chart showing the comparison of antibody targeted cage (anti-CD22 HSPC cage) and non-targeted cage (HSPC only) binding to mCD22Ig.

The invention provides a targeted nanoparticle drug delivery system for the treatment of B-cell malignancies, e.g., B cell lymphomas, leukemias and autoimmune disorders. The targeted nanoparticle drug delivery system is assembled from four components which include a viral capsid protein (C protein) from Hepatitis B, a lipid, a cytotoxic agent and a targeting moiety.

Lymphomas are categorized by how the B-cells are affected. B-cell lymphomas include for example, Follicular lymphomas; Small Non-Cleaved Cell Lymphomas (e.g., Endemic Burkitt's lymphoma, Sporadic Burkitt's lymphoma and Non-Burkitt's lymphoma); Marginal Zone Lymphoma (e.g., Mucosa-Associated Lymphoid Tissue MALT/MAL-Toma (extranodal, Monocytoid B-cell lymphoma (nodal) and Splenic Lymphoma with villous lymphocytes); Mantle Cell Lymphoma; Large Cell Lymphoma (e.g., Diffuse Large Cell, Diffuse Mixed Cell, Immunoblastic Lymphoma Primary Mediastinal B-Cell Lymphoma and Angiocentric Lymphoma—Pulmonary B-Cell); and Small Lymphocytic Lymphoma.

B cell leukemias include for example, small lymphocytic/B cell chronic lymphocytic leukemia (SLL/B-CLL ALL-L3 (Burkitt's type leukemia), chronic lymphocytic leukemia (CLL), and acute lymphoblastic leukemia.

Autoimmune disease includes any autoimmune disease wherein elimination or depletion or inhibition of the activity or proliferation of B cells is therapeutically beneficial. Such autoimmune diseases will include in particular T and B cell mediated autoimmune diseases. Examples include, the treatment or prevention of autoimmune, inflammatory, proliferative and hyperproliferative diseases, and of cutaneous manifestations of immunologically mediated diseases (e.g., rheumatoid arthritis, lupus erythematosus, systemic lupus erythematosus, Hashimoto's thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, lichen planus, pemplugus, bullous pemphigus, epidermolysis bullosa, urticaria, angioedemas, vasculitides, erythema, cutaneous eosinophilias, or Alopecia areata); the treatment of reversible obstructive airways disease, intestinal inflammations and allergies (e.g., inflammatory bile disease, Coeliac disease, proctitis, eosinophilia gastroenteritis, mastocytosis, Crohn's disease and ulcerative colitis), food-related allergies (e.g., migraine, rhinitis and eczema), and other types of allergies.

The targeting moiety is a B-cell specific targeting moiety. The targeting moiety selectively targets normal B-cells (i.e., non-cancerous) or transformed B-cells (i.e., cancerous). For example, a B-cell specific targeting moiety is a compound that binds to a B cell surface marker, B cell antigen or certain members of the Fc Receptor family. Exemplary B cell surface markers include the CD10, CD19, CD20, CD21, CD22, CD23, CD24, CD37, CD52, CD53, CD72, CD73, CD74, CDw75, CDw76, CD77, CDw78, CD79a, CD79b, CD80, CD81, CD82, CD83, CDw84, CD85 and CD86 leukocyte surface markers. A preferred B cell surface marker is preferentially expressed on B cells compared to other non-B cell tissues of a mammal and may be expressed on both precursor B cells and mature B cells. Most preferably the B-cell surface marker is CD22. CD22 is also known as "BL-CAM" and "LybB" and is involved in B cell signaling and cell-cell adhesion.

The B-cell specific targeting moiety is an antibody or fragment thereof. As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, CDR-grafted, chimeric, single chain Fv, nanobodies, domain antibodies (dAbs), $F_{ab}$, $F_{ab'}$, and $F_{(ab')2}$ fragments.

Alternatively, the B-cell specific targeting moiety is a non-natural ligand, e.g., an antibody mimetic. A B-cell specific mimetic is an agent that is capable of binding a B-cell surface marker or antigen with an affinity and specificity similar to those of an antibody. Mimetics include for example, polypeptides derived from natural protein scaffolds, such as lipocalins, β-pleated sheets, A domains, etc. Microproteins are derived through mutagenesis of small cysteine-rich domains, which occur naturally in many proteins, in particular, in toxins from a variety of venomous species, including snakes, scorpions, spiders, snails and anemones. Microproteins are typically small (35-55 amino acids), cysteine rich (cysteines constitute at least 15% of the total amino acid composition) and nonimmunogenic. Microproteins can also be engineered to have long circulating half-lives, similar to those of antibodies, by the addition of peptides that bind to immunoglobulin or serum albumin in the circulation. Thus, they provide many of the advantages of antibodies for specific targeting but also offer superiority in terms of cost of manufacturing, due to their small size. Small molecules include, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organomettallic compounds) having a molecular weight less than about 5,000 grams per mole, organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A cytotoxic agent is any agent that is capable of killing a cell. A cytotoxic agent is for example a chemotherapeutic agent, a toxin (e.g., an enzymatically active toxin of bacterial, fungal, plant, or animal origin, or fragments thereof), a radioactive isotope (e.g., a radioconjugate), or an antisense or iRNA molecule that suppresses the synthesis of proteins essential for cell survival. Chemotherapeutic agents include for example, cyclophosphamide, doxorubicin, vincristine, prednisone, busulfan, cisplatin, methotrexate, daunorubicin, melphalan, cladribine, vinblastine, auristatin, bleomycin, calicheamycin, and chlorambucil. Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclotides are available for the production of radioconjugate. Examples include, $^{212}$Bi, $^{131}$I, $^{131}$In, $^{90}$Y, and $^{186}$Re. RNA molecules that inhibit protein synthesis, either through promoting RNA degradation or through inhibiting translation, include antisense RNA, siRNA, and double stranded RNA (dsRNA).

Nanocage

The nanocage that surrounds the drug or therapeutic compound is constructed from the Hepatitis B Virus (HBV) core protein (C-protein) (SEQ ID NO. 1), HBV C-protein is a protein that naturally self-assembles to form the protein capsid of the virus and is 183 amino acids in size with a high concentration of positively charged amino acids at the C-terminal end that dangle into the interior of the capsid when assembled. This dangling tail can be engineered in many ways so as to specifically interact with molecules of a given characteristic. For example, the natural state of the protein has a cluster of positive charges at this end that can interact with negatively charged molecules such as DNA or RNA. Alternatively, the C-protein can be engineered so that the C-terminal tail has a cluster of negative charges (Asp or Glu residues) that can interact with positively charged molecules. Further, the C-protein can be engineered to form a fusion protein with a toxin or protoxin.

```
SEQ ID NO. 1:
Hepatitis Core Pntigen: protein sequence 1 to 183:
MET ASP ILE ASP PRO TYR LYS GLU PHE GLY  (10)

ALA THR VAL GLU LEU LEU SER PHE LEU PRO  (20)

SER ASP PHE PHE PRO SER VAL ARG ASP LEU  (30)

LEU ASP THR ALA SER ALA LEU TYR ARG GLU  (40)

ALA LEU GLU SER PRO GLU HIS CYS SER PRO  (50)

HIS HIS THR ALA LEU ARG GLN ALA ILE LEU  (60)

CYS TRP GLY GLU LEU MET THR LEU ALA THR  (70)

TRP VAL GLY ASN ASN LEU GLU ASP PRO ALA  (80)

SER ARG ASP LEU VAL VAL ASN TYR VAL ASN  (90)

THR ASN MET GLY LEU LYS ILE ARG GLY LEU (100)

LEU TRP PHE HIS ILE SER CYS LEU THR PHE (110)

GLY ARG GLU THR VAL LEU GLU TYR LEU VAL (120)

SER PHE GLY VAL TRP ILE ARG THR PRO PRO (130)

ALA TYR ARG PRO PRO ASN ALA PRO ILE LEU (140)

SER THR LEU PRO GLU THR THR VAL VAL ARG (150)

ARG ARG GLY ARG SER PRO ARG ARG ARG THR (160)

PRO SER PRO ARG ARG ARG ARG SER GLN SER (170)

PRO ARG ARG ARG ARG SER GLN SER ARG GLU (180)

SER GLN CYS
```

HBV core protein assembles to form an icosahedral subviral capsid. The full length core protein forms (T=4) particles with a diameter of 36 nanometers (Crowther R A et. al., Three-dimensional structure of hepatitis B virus core particles determined by electron cryomicroscopy, Cell 77:943-50, 1994). Inside this particle, the final 40 amino acids of the core protein are thought to interact with the genomic DNA of the virus. Core protein constructs lacking this putative DNA-binding region also form icosahedral capsids, but with a triangulation number of 3 (T=3). Interactions between core protein monomers in these two types of capsids are thought to be similar.

In HBV capsids, C-protein monomers form dimers which associate tightly via a "spike." The spike is a central four alpha-helical bundle (Bottcher B et. al., Determination of the fold of the core protein of hepatitis B virus by electron cryomicroscopy, Nature 386:88-91, 1997) with a 2-fold axis of symmetry. The icosahedral subviral particle consists of 120 C-protein dimers assembled around 5-fold and 6-fold axes in a rough head-to-tail type interaction. In the mature virus, the tips of the central spikes of the 120 dimers are oriented close the surface of the particle where it is coated by a plasma membrane envelope.

Mutation in the HBV C-protein is introduced to confer specific functional properties to the nanoparticles. For example, the HBV C-protein is mutated in the spike area of the dimer or the interface between dimers. Mutations in the spike are used to introduce functional groups at the surface of the capsid in order to promote envelopment by a plasma membrane. In addition, a "protease recognition loop" is engineered in the spike to facilitate the breakdown of the entire capsid once it reaches the bloodstream. Mutations in the interface will stabilize the capsid as to "tune" the lifetime of the capsid prior to disassembly.

In order to attach functional groups, either the amino acid cysteine or the amino acid lysine will be placed at the tip of the spike in such a way as to protrude away from the capsid surface toward the plasma membrane envelope. Three positions (77, glutamic acid to cysteine; 78, aspartic acid to cysteine; and 80, alanine to cysteine) have been identified for the introduction of these amino acids which will be functionalized at a later stage. The choice of lysine or cysteine at each position was dependent of the orientation and geometry of each amino acid as judged from the crystal structure (Wynne S A et. al., The crystal structure of the human hepatitis B virus capsid, Molecular Cell 3:771-80, 1999) of the HBV capsid. With the 2-fold symmetry of the 4-helical bundle, an introduction of one reactive amino acid at each single position will give a total of two bioconjugated molecules per spike.

At the interface between monomers, pairs of cysteines will be introduced in such a way that they will promote and strengthen the assembly. The first cysteine (e.g. amino acid 23) is introduced in the first position in order to disulphide bond with the second position (amino acid 132 in this case) in a neighboring molecule. Similarly, the second position will also participate in a disulphide bond, allowing the dimer to participate in four disulphide bridges and a total of 180 stabilizing covalent interactions. Four different types of disulphide bonds (Table 1), which may be combined according to their effectiveness in stabilizing the assembly and the desired strength of the assembly will be created.

TABLE 1

Dual Cysteine Mutants

Phenylalanine 23 to cysteine; threonine 132 to cysteine
Aspartic acid 29 to cysteine; arginine 127 to cysteine
Threonine 33 to cysteine; valine 124 to cysteine
Leucine 37 to cysteine; valine 120 to cysteine Once an HBV-derived particle has traveled into a cell, it is necessary for it to dissolve into its component monomers so that it can release its therapeutic cargo. To expedite this process, the spike-forming region of the monomer is engineered to contain a lysosomal protease-recognition sequence. The protease will recognize and cleave this loop and thereby promote disassembly. The most common lysosomal proteases are the cathepsins, aspartate proteases, and zinc proteases.

The recombinant C-protein will be expressed and purified using common molecular biology and biochemistry techniques. The C-protein gene in an expression plasmid is available from commercial vendors. Expressed C-protein in solution forms a dimer that is naturally stabilized by specific salt bridges, hydrophobic interactions, and covalent inter- and intramolecular disulfide bonds. The intramolecular bonds will be engineered so that C-protein stability can be tuned to a desired level. In addition, intermolecular disulfide bonds will be engineered so as to tune the stability of the cage. Specific salt bridges between dimers that help form the capsid can be mutated to cysteines so that disulfide bonds can form and help stabilize the capsid structure. All modifications of C-protein are based on an extensive analysis of the capsid crystal structure and energy minimization models performed on electron density maps derived from structural data.

The C-protein will also be engineered so as to contain protease recognition sites at hinge and loop regions. The immunodominant spike of the C-protein can accommodate insertions of up to 46 residues and still be able to form capsids. Recognition sites for cathepsins, aspartate proteases, or zinc proteases will be inserted into the spikes. These recognition sites add the benefit of quick degradation of the building blocks after the entire system has started to fall apart as a time-release method of releasing the toxins into the intracellular milieu. Keeping the nanocages intact until they enter the cell will minimize the possibility of an immune response to the presence of "naked" C-protein in the blood stream.

Alternatively, the C-protein is genetically altered such that the C-terminal tail is replaced with the protein therapeutic of choice. This will be engineered at the genetic level so as to create a chimeric building block of C-protein and the therapeutic protein (fusion protein). The therapeutic protein will be linked to the C-protein by a tether of amino acids that codes for a specific protease recognition site. This will allow the protein therapeutic to be freed after the cage begins to fall apart. Another option for specifically attaching a protein therapeutic is to mutate a cysteine residue into the C-protein tail. A matching cysteine residue will be placed on the protein therapeutic of choice. This will create a disulfide bond between the C-protein and the protein therapeutic.

At the region of the protein that forms the outer spikes of the capsid, cysteine residues will be engineered in so that a modified Hepatitis B Virus S-protein can be covalently linked. S-proteins will be modified to have cysteines as well to complement the disulfide bridge formation between C-protein. The S-protein guides the lipid bi-layer formation.

Also as an option, instead of using S-protein, a small peptide with similar characteristics could be used to guide envelopment of the cage. A sequence that could replace S-protein would have a flexible region that ends with a cysteine so as to form disulfide bridges with the cage. The other end of the peptide will be composed primarily of hydrophobic residues. An example of such a peptide is below in SEQ ID NO. 2. The hydrophobic region of this peptide will associate with the hydrophobic lipid bi-layer region, thus acting to guide the formation of a tight vesicle around the cage. These peptides are then added to the reaction mix after the formation of the cage and disulfide link to the C-protein.

SEQ ID NO. 2: HBV S-protein alternative peptide:
CYS ALA ARG GLY ALA ARG GLY ALA ARG GLY ALA ARG GLY ILE LEU GLY VAL PHE ILE LEU LEU TYE MET As an alternative to use of the S-protein or equivalent peptides described above, phospholipids can be directly linked to the C-protein core. At the apex of the spike region of core protein a cysteine residue will be mutated as above. At this site fatty acids such as a modified phosphatidyl serine can be covalently attached. These fatty acids can act as a guide for other phospholipids and cholesterols to form a bilayer around the nanocage. This replaces the necessity of S-protein or the previously discussed transmembrane engineered peptide. Also with the addition of these covalently attached phospholipids to the spike region (also known as the immunodominant spike), immune responses are expected to be significantly repressed.

Assembly of the Nanocage and Drug Capturing

Core proteins in a mildly buffered solution are introduced to the therapeutic compound (e.g., cytotoxic agent or drug) of choice. Therapeutic molecule:C-protein complexes form in just a few seconds as dictated by the general physics of molecular diffusion and coulombic attraction. To initiate the self-assembly reaction of the capsid, the ionic strength of the solution is then elevated by the addition of NaCl to a final concentration of 0.6 M. After incubating the reaction for one hour the presence of fully formed capsids will be verified using standard biochemical analyses. Next the cage will be mixed with either the re-engineered S-protein or with an engineered peptide as mentioned above. These additions will covalently link to a complementary cysteine on the surface of the cage at the spike of each building block.

Bioconjugation of Functionalized Phospholipids to Proteins

Phospholipids can be incorporated into a protein matrix, the most stable of which involves covalently combining a phospholipid to a functional group found on the side chains of specific amino acids within the protein. In the two similar protocols presented, heterobifunctional cross-linking molecules are utilized in order to provide a wide template for which many different functional groups found on different amino acids can be utilized, with the goal of optimizing distance constraints, solvent interactions, combinations of amino acid residue functional groups and phospholipids, and simplicity of synthesis.

Sulfhydryl functional groups will be specifically engineered into the core proteins. Through these functional groups, phospholipid molecules can then be anchored which will guide the enveloping process and form the liposome.

The use of heterobifunctional cross-linking molecules allows the possibility of engineering different functional groups at appropriate anchor points along the core protein matrix while using the same phospholipid precursors, if that is a necessary step. For example, sulfhydryl functional groups are also involved in stabilizing the intermolecular interactions between core proteins that will stabilize the core cage. If utilizing the same functional group for anchoring phospholipids prevents the specific interaction of engineered sulfhydryl functional groups to form intermolecular bonds and therefore negatively impact the stability of the core protein shell, then other functional groups such as hydroxyl and amine groups can be engineered into the protein at locations where phospholipid anchoring is specifically designed. This merely requires re-engineering the core proteins at a single location, and the use of an alternative, commercially-available heterobifunctional cross-linking molecule.

Preparation of the Lipid Bi-Layer Envelope and Envelopment of the Nanocage

The envelope is a cationic or anionic lipid bilayer. A homogeneous mixture of various ratios of lipids (predominately phospholipids) and cholesterol will be made by adding dried components to a solution of chloroform: methanol (2:1 by volume). For example, 100 mg of phosphatidyl choline, 40 mg of cholesterol, and 10 mg of phosphatidyl glycerol are added to 5 mL of chloroform methanol solution. This mixture is gently shaken to thoroughly mix all components. Next the mixture is dried down so as to remove all organic solvents. This dried mixture is now introduced to a few milliliters of aqueous solution (buffered $H_2O$) and mechanically dispersed by sonication. This solution is quickly added to a suspension of fully assembled nanocages containing captured therapeutic compound. The nanocages will already have been covalently modified with either envelopment enhancing peptides (engineered or protein-S) or with phospholipids. After a brief incubation with gentle mixing, enveloped cages are separated and purified using simple centrifugation and size exclusion chromatography.

Modification of the Envelope

Optionally, functional groups are added to the envelope of the delivery system. The functionalities (e.g., B cell targeting moieties, cholesterol moieties, transduction domains) allow the delivery system to be specifically targeted and delivered to a cell type, e.g., B cells, pass through cell walls and/or evade the immune system. Transduction domains include the Human Immunodeficiency Virus (HIV) transactivator of transcription (TAT) peptide or poly-arginine. To anchor the transduction domains in the lipid bilayer they are tagged with cholesterol. Transduction domains may be particularly useful in allowing intracellular entry when the B cell targeting moiety targets a cell surface molecule that does not readily internalize, e.g. CD20.

Method of Use

The growth of cells are inhibited or cell death is induced by contacting a cell, with a composition containing the drug delivery system according to the invention. The cell is contacted in vivo, ex vivo or in vitro. The cell is further contacted with one or more addition cytotoxic agents. Suitable cytotoxic agents are know in the art and include those described herein. By inhibition of cell growth is meant the cell proliferates at a lower rate or has decreased viability compared to a cell not exposed to the composition. Cell growth is measured by methods know in the art such as, the MTT cell proliferation assay. The cell is a B-cell or any cell that expresses CD22. The cell is a tumor cell such as a leukemia or lymphoma.

Patients with tumors, e.g. lymphomas or leukemia or autoimmune disease are treated by administering the drug delivery system according to the invention. The drug delivery systems are useful as a primary method of treating cancers or autoimmune disease, as wells as in augmenting previously-known methods of treatment such as immunotherapy, chemotherapy and radiation therapy.

The terms "treating" and "treatment" as used herein refer to reduction in severity and/or frequency of symptoms, elimination of symptoms and/or underlying cause, prevention of the occurrence of symptoms and/or their underlying cause (e.g., prophylactic therapy), and improvement or remediation of damage. Treatment is efficacious if the treatment leads to clinical benefit such as, a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor or autoimmune disease. Efficaciousness is determined in association with any known method for diagnosing or treating the particular tumor type.

By the terms "effective amount" and "therapeutically effective amount" of a compound of the invention is meant a nontoxic but sufficient amount of the drug or agent to provide the desired effect.

By "patient" is meant any animal for which treatment is desirable. Patients may be mammals, and typically, as used herein, a patient is a human individual.

Patients are identified by standard methods of the particular tumor type or autoimmune disease. Lymphomas are diagnosed for example, by biopsy, blood tests, CAT or PET Scan, MRI or immunohistochemistry. Leukemia is diagnosed for example, by bone marrow biopsy, blood tests or lumbar puncture. Autoimmune diseases are diagnosed generally by the presence of anti-nuclear antibodies.

A drug delivery system is formulated in a pharmaceutically acceptable carrier. By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

The drug delivery system can be administered directly to a patient or in pharmaceutical compositions in which it is mixed with a suitable carrier, excipient and/or any of the other additives described herein. The drug deliverys system may also be administered in combination with one or more additional active agents, in which case they may be administered separately, in different dosage forms, or simultaneously, either in one dosage form or in two different dosage forms. Combination therapy is especially desirable when the drug delivery system and the additional active agent(s) exhibit synergistic effects in the patient. "Synergy" describes instances wherein the therapeutic effects of a plurality of active agents, when administered in combination, is greater than the simple summation of the therapeutic effects of the active agents when administered alone. Such synergistic effects are readily determined using known methods of testing pharmaceutical compositions such as those disclosed herein. Combination therapy of particular interest involves administering drug delivery system in conjunction with conventional chemotherapy, radiation, immunotherapy or bone marrow transplant.

Toxicity and therapeutic efficacy of the compositions described herein can be determined by standard pharmaceutical procedures in cell cultures or experimental animals, e.g., procedures used for determining the maximum tolerated dose (MTD), the $ED_{50}$, which is the effective dose to achieve 50% of maximal response, and the therapeutic index (TI), which is the ratio of the MTD to the $ED_{50}$. Obviously, compositions with high TIs are the most preferred compositions herein, and preferred dosage regimens are those that maintain plasma levels of the drug delivery system and/or additional active agents from the compositions at or above a minimum concentration to maintain the desired therapeutic effect. Dosage will, of course, also depend on a number of factors, including the desired effect of the composition, the particular active agents present, the site of intended delivery, the route of administration, and other pertinent factors known to the prescribing physician. Generally, however, dosage will be in the range of approximately 0.1 µg/kg/day to 100 mg/kg/day, more typically in the range of about 1.0 mg/kg/day to 10 mg/kg/day.

Administration of the compositions described herein may be carried out as part of a treatment regimen that may include multiple instances of administration of drug delivery system as well as administration of other pharmaceutically active compositions. Such a regimen may be designed as a method of treatment for any of the diseases or conditions described herein, and/or as a method of long-term maintenance of the health of a patient after having been treated for any of the diseases or conditions described herein (e.g., preventing recurrences).

Administration of the compositions described herein may be carried out using any appropriate mode of administration and dosage form. Thus, administration can be, for example, oral, ocular, parenteral, transdermal, transmucosal, sublingual, by inhalation, or via an implanted reservoir in a dosage form. The term "parenteral" as used herein is intended to include, for example, subcutaneous, intravenous, and intramuscular injection. The term "transmucosal" as used herein is intended to include, for example, rectal, vaginal, buccal, sublingual, and penile administration. The term "inhalation" as used herein is intended to include inhalation via the nose or the mouth, and includes instances wherein absorption of the composition occurs in the lungs as well as, for example, the mucosal membranes of the mouth, nose, and throat. Administration via implants is meant to include implants affixed anywhere on or positioned anywhere inside the body, including within body cavities (e.g., intraperitoneal implants, intraocular implants, implants in joints, etc.), within organs, and subcutaneously.

Depending on the intended mode of administration, the pharmaceutical composition may be a solid, semi-solid, or liquid such as, for example, a tablet, a capsule, a caplet, an aerosol, a liquid, a suspension, an emulsion, a cream, a gel, a suppository, granules, pellets, beads, a film, a powder, a sponge, or the like.

In one embodiment, the composition comprises a unit dosage form suitable for single administration of a precise dosage. In another embodiment, the composition comprises a reservoir such as in an implant capable of controlled delivery of the composition over time.

Suitable pharmaceutical compositions and dosage forms may be prepared using conventional methods known to those in the field of pharmaceutical formulation and described in the pertinent texts and literature, e.g., in Remington: *The Science and Practice of Pharmacy* (Easton, Pa. Mack Publishing Co., 1995). A description of some, but not all, of the suitable dosage forms is provided infra.

Preparations according to this disclosure for parenteral administration include sterile aqueous and nonaqueous solutions, suspensions, and emulsions. Injectable aqueous solutions contain reversine in water-soluble form. Examples of nonaqueous solvents or vehicles are described supra. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable compositions are rendered sterile by incorporation of a sterilizing agent, filtration through a bacteria-retaining filter, irradiation, or heat. They can also be manufactured using a sterile injectable medium. Any active agents present in the compositions may also be in dried, e.g., lyophilized, form that may be rehydrated with a suitable vehicle immediately prior to administration via injection.

The invention will be further illustrated in the following non-limiting examples.

Example 1

Core Protein Expression and Purification

Protocol 1: A pET-11a vector containing the full-length core protein gene, is transformed into *E. coli* DE3 cells and grown at 37° C. in LB media, fortified with 2-4% glucose, trace elements and 200 µg/mL carbenicillin. Protein expression is induced by the addition of 2 mM IPTG. Cells are harvested by pelleting after three hours of induction. SDS-PAGE is used to assess expression. Cells are resuspended in a solution of 50 mM Tris-HCL, pH 7.4, 1 mM EDTA, 5 mM DTT, 1 mM AEBSF, 0.1 mg/mL DNase1 and 0.1 mg/mL RNase. Cells are then lysed by passage through a French pressure cell. The suspension is centrifuged at 26000×G for one hour. The pellet is discarded and solid sucrose is added to the supernatant to a final concentration of 0.15 M. The supernatant is then centrifuged at 100000×G for one hour. The pellet is discarded and solid $(NH_4)_2SO_4$ is then added to a final concentration of 40% saturation. The supernatant is then stirred for one hour and centrifuged for one hour at 26000×G. The pellet is resuspended in a solution of 100 mM Tris-HClLat pH 7.5, 100 mM NaCL, 50 mM sucrose and 2 mM DTT (Buffer A) and loaded onto a Sepharose CL-4B (Pharmacia Biotech, Piscataway, N.J.) column (5 cm diameter×95 cm) equilibrated with Buffer A. The column is eluted at 2 mL/minute. HBV viral capsids can be well separated from large aggregates and from soluble proteins of lower molecular weight. The fractions are pooled according to chromatographic profile and SDS-PAGE analysis and the solution concentrated by ultrafiltration using Diaflo YM 100 ultrafitration membrane (Amicon, Beverly, Mass.) to about 10 mg/mL. Concentrated protein is dialyzed against 50 mM Tris-HCL, pH 7.5 and 0.15 M sucrose. The solution is then adjusted to pH 9.5 with ION NaOH and urea is added to a final concentration of 3.5 M. The solution is then filtered using a Millex-HA 0.45 µm pore size filter unit (Millipore, Bedford, Mass.) and applied to a column (6.0 cm diameter×60 cm) of Superdex 75 (Pharmacia Biotech, Piscataway, N.J.) equilibrated with 100 mM sodium bicarbonate, pH 9.5, containing 2 mM DTT. The column is eluted at 5 mL/minute. The fractions containing dimeric protein as assessed by SDS-PAGE are pooled. These procedures will be used for the expression and purification of all core protein mutants. Alternatively, the expression of this protein can be done in yeast cells.

Protocol 2:
Starter Culture

The PET vector containing the gene for 77 C His-tagged Core Protein is transformed in BL21 (DE3) PlysS cells for expression. The starter culture is inoculated from a colony on a 1× Luria Broth (1×LB)—agarose plate or from a 10% glycerol stock, stored at −80° C. 1×LB is autoclaved in a 2 L flask and allowed to cool. 100 mg of ampicillin (Amp) is added and the culture is inoculated. Cells are allowed to grow for 24 hours with shaking at 225 RPM at 37° C.

Cell Growth and Isolation:

15 2 L flasks with 0.8 L of 2× yeast-tryptone (2XYT) broth are autoclaved. 1 ml of 100 mg/ml ampicillin is added to each flask. 20 mL of starter culture is then added to each flask. The cultures are incubated at 37° C., shaking at 225 rpm until OD reaches 0.4 at 600 nm. This process takes approximately 3 hours. When OD reaches 0.4, protein expression is induced with 1 ml of 1 M IPTG. The cultures are incubated for an additional 4 hours with shaking or until the OD reaches 2.0 or greater. Cells are harvested by centrifuging in 500 mL centrifuge bottles at 8000 RPM for 10 minutes. Bacterial pellets are transferred into 50 mL falcon tubes and stored at at −20° C.

Cell Disruption

Bacterial pellets are thawed in a 50 ml tube (approximately 20 to 30 ml). 20 ml resuspension buffer (4 M Urea, 50 mM $NaHCO_3$ (pH 9.5), 10 mM imidazole) is added to the cell paste. An additional 20 mls of resuspension buffer is added and the solution is stirred until cells are resuspended into a roughly homogenous solution. Cells can also be resuspended by repeatedly pipetting them with a 10 ml pipette.

The beaker containing resuspended cells is placed in an ice bath. Using a Branson probe sonicator on pulse mode at approximately 40% cycling, and power setting of approximately 4 to 5, the suspension is sonicated for 5 minutes. The cell mixture is sonicated in several intervals, allowing it to rest on ice in between if it appears that the sample may be heating to higher than room temperature. The cell lysate is removed from ice, and 100 µL of 100 mg/mL DNase is added to the suspension. This suspension is swirled occasionally and allowed to stand for 10 minutes and then returned to the ice. The sonication step is repeated for 5 more minutes. The cell suspension is transferred to plastic centrifuge tubes and centrifuged at 15,000 RPM for 40 minutes. The supernatant is decanted and saved.

Nickel Column Purification

The nickel column is washed and equilibrated in the resuspension buffer. Centrifuged cell lysate is load onto the column, and protein solution is allowed to sink to the top of the nickel matrix. The column is washed with 50 mL of resuspension buffer followed by 250 mL of wash buffer (4 M Urea, 50 mM $NaHCO_3$ (pH 9.5), 20 mM imidazole). The protein is eluted using 200 mL of elution buffer (4 M Urea, 50 mM $NaHCO_3$ (pH 9.5), 250 mM imidazole) Aliquots are collected every 20 mL.

Measure Concentration and Dialysis:

The absorbance of the aliquots is measured to detect for presence and/or concentration of protein. Polyacrylamide gel electrophoresis (PAGE) analysis is performed on protein-containing aliquots to determine purity. Fractions containing the Cp Block1 protein are collected and transferred to dialysis tubing. The protein is dialyzed with storage buffer (4 M Urea, 20 mM $NaHCO_3$ (pH 9.5)) for 8 to 12 hours at 4° C. Dialysis is repeated once. Pure dialyzed protein is stored at −20 C.

Example 2

Delivery System Formation

The delivery system is formed using the following protocol:
Encapsulation
Add beta-mercaptoethanol (BME) to protein solution to get final concentration of 5 µM. Filter with 0.22 µm PES filter (Nalgene).
A. If encapsulating Doxorubicin HCl (DOX), or other small molecule therapeutic agent, predissolved encapsulate is added in $ddH_2O$ to protein solution to obtain a final DOX concentration of 0.5 mg/mL. This solution is kept in a water bath set to 25° C. for 12 hours.

B. If encapsulating siRNA, siRNA-containing solution is added to the protein solution at a 3150× molar excess (nucleic acid:protein monomer). 0.5 M NaCl is added to solution to obtain final NaCl concentration of 100 mM. This solution is kept in a water bath set to 25° C. for 12 hours.

First Fast Performance of Liquid Chromatography (FPLC) Purification:

The cage material is purified via FPLC (Amersham Pharmacia). The large FPLC column (Pharmacia XK-26 26 mm×1000 mm) can be run at 1.5 mL/min running 0.5×PBS pH 9.4 buffer as the mobile phase and Sepharose CL-4B (Amersham Pharmacia) matrix as the stationary phase. Delivery system fractions are collected, combined, and run on a gel (SDS-Page; Biorad) to determine the delivery system concentration versus protein standards (usually made with just CpB1 protein in dialysis buffer). The protein concentration is cross referenced with an absorbance measurement at 280 nm. The protein solution is then concentrated to 1.0 mg/mL via the Amicon filtration system.

Production of Lipid Enveloping Material (LEM):

Cholesterol (Avanti Lipids, Alabaster, Ala., USA) and L-α-Phosphatidylcholine, Hydrogenated Soy (HSPC, Avanti Lipids, Alabaster, Ala., USA) and DiI 1,1'-Dioctadecyl-3,3,3',3'-tetramethylindocarbocyanine perchlorate (DiI, Sigma Aldrich, St. Louis, Mo. USA) are premixed in a 31.9:15.6:1 molar ratio, respectively, as dry powders in a glass beaker. The mixture is then dissolved and homogenized with 2.0 mL of chloroform. Once homogenized, the chloroform is evaporated off (20 to 30 minutes on a hot plate set to 50° C.). Once dry, 0.5×PBS is added to make the LEM at a concentration of 0.2 mg/mL. This solution is then probe sonicated (240 seconds, power level=7, cycle=50%). The aqueous LEM solution is then mixed at 70° C. for an additional 30 minutes.

Functionalizing Protein with Maleimide-Terminated Lipid:

The raw cage solution is treated with TCEP tris-carboxyethylphosphine (TCEP) as a dry powder in a 4-fold molar excess compared to the protein concentration (1 exposed sulfhydryl per CpB1 protein; 240 exposed sulfhydryls per cage). 1,2-Dipalmitoyl-sn-Glycero-3-Phosphoethanolamine-N-[4-(p-maleimidophenyl)-butyramide] (Sodium Salt) (PE-MAL) is added in 3× molar excess predissolved in 500 μL dimethylformadmide (DMF) dropwise to the raw cage solution. The PE-MAL is allowed to react with the raw cage for 60 seconds.

Enveloping and Purifying the Functionalized Cage, And Purify via FPLC:

The LEM solution is added to the functionalized cage solution at a mass ratio of 1:3. The solution is allowed to mix and homogenize for 60 minutes by stirring and heating on hot plate at 60° C. It is then filtered once with 0.45 μm Whatman PES filter (almost all of the material should pass easily through the filter). It is then filtered again with a 0.22 μm Nalgene PES filter (again, almost all of the material should pass through the filter relatively easily). The material is then purified via FPLC with 0.5×PBS buffer, pH 9.4. Again, the enveloped cage elutes from 220 to 280 mL. Fractions are collected and the delivery system size is verified via dynamic light scattering (Dynapro Titan, Wyatt Instruments, Goleta, Calif.). Protein concentration is determined by SDS-Page gels.

Example 3

Production of Targeted Delivery System

The targeted delivery system is produced using the following protocol.

Antibody Modification for Delivery System Coupling

Antibodies at a concentration of 4 mg/mL in 1×PBS buffer pH 7.4 are treated with 20 molar equivalents of Trauts reagent, 2-iminothiolane HCl, for 1 hour. The antibodies are purified via column chromatography on a 8×200 mm G-50 (Amersham Pharmacia) in 0.25×PBS buffer pH 7.4.

Delivery System Modification with Antibodies:

The delivery system is treated with 200 mole equivalents of PE-maleimide lipid (1,2-Dipalmitoyl-sn-Glycero-3-Phosphoethanolamine-N-[4-(p-maleimidophenyl)-butyramide] (Sodium Salt)) (dissolved in DMF) per mole equivalent of delivery system. Upon standing for 30 minutes the delivery system, 1 mole equivalent, is treated with 30 mole equivalents of antibodies modified with Trauts reagent (the above step). This solution is allowed to react overnight. Excess antibodies are removed from the antibody targeted system via a column (16×200 mm) packed with Sepharose CL-4B matrix with the isocratic mobile phase (0.25×PBS pH 7.4). This gives a typical yield of 60% with 20-30 antibodies per delivery system determined by SDS-PAGE gels.

Example 4

Protocol for PE Conjugation via SMPB Intermediate

The following protocol is used to conjugate PE via an SMPB intermediate: 100 micromoles of phosphatidyl ethanolamine (PE) is dissolved in 5 mL of argon-purged, anhydrous methanol containing 100 micromoles of triethylamine (TEA). The solution is maintained over an argon or nitrogen atmosphere. The reaction may also be done in dry chloroform50 mg of succinimidyl-4-(p-maleimidophenyl)butyrate (SMPB, Pierce) is the added to the PE solution, and the solution is mixed well to dissolve. The solution is allowed to react for 2 hours at room temperature, while maintaining it under an argon or nitrogen atmosphere. Methanol is removed from the reaction solution by rotary evaporation and the solids are redissolved in 5 mLchloroform. The water-soluble reaction by-products are extracted from the chloroform with an equal volume of 1% NaCl. Extraction is repeated once more. The MPB-PE derivative is purified by chromatography on a column of silicic acid (Martin F J et al., Immunospecific targeting of liposomes to cells: A novel and efficient method for covalent attachment of Fab' fragments via disulfide bonds. Biochemistry, 1981; 20:4229-38). Chloroform is removed from the MBP-PE by rotary evaporation. The derivative is stored at −20° C. under a nitrogen atmosphere until use.

Example 5

Protocol for PE Conjunction Via MBS Intermediate

The following protocol is used to conjugate PE via an MBS intermediate: 40 mg of PE is dissolved in a mixture of 16 mL dry chloroform and 2 mL dry methanol containing 20 mg triethylamine, maintained under nitrogen. 20 mg of m-maleimidobenzoyl-N-hydroxysuccinimide ester (MBS) is added to the lipid solution and mixed to dissolve. The solution is allowed to react for 24 hours at room temperature under nitrogen. The organic phase is washed three times with PBS, pH 7.3, to extract excess cross-linker and reaction by-products The organic solvents are removed by rotary evaporation under vacuum.

Example 6

Protocol for Conjugating Maleimide-Containing Intermediates (MCI) to Sulfhydryl Containing Proteins (SCP)

The following protocol is used to conjugated MCI to SCP: The SCP is dissolved in Tris-HCl buffer (pH=8.0, 100 mM) to obtain a concentration of 1 mM). The solution is purged under a nitrogen or argon atmosphere for 20 minutes. MCI is dissolved in the same buffer as above and also purged under a nitrogen or argon atmosphere for 20 minutes, to obtain a 10-fold molar excess. The two solutions are combined, and the solution is further purged under a nitrogen or argon atmosphere for an additional 20 minutes. The reaction is allowed to proceed for 6 hours, at room temperature.

Example 7

Evaluation of Target Specificity: Fluorescent Cage Binding Protocol 96-well ELISA plates are coated with either 50 µL of mCD22Ig protein or 2% BSA (w/v) in 0.1 M borate buffered saline at a concentration of 50 µg/ml overnight. Plates are then washed three times in Tris buffered saline (TBS). All wells are then blocked with 2% BSA in TBS for one hour, followed by three TBS rinses. Anti-CD22 targeted cage constructs and non-targeted cage constructs (no antibody) containing 4% DiI embedded within the lipid envelope are incubated in triplicate, at multiple concentrations, in buffer containing 2% BSA and 0.1% Tween in TBS for 4 hours. Wells are then rinsed four times in TBS and plates are read using a Typhoon Molecular Imager (Molecular Dynamics). Background wells contain mCD22Ig (from original plating) and TBS. Fluorescent reads are conducted in TBS, and averaged; standard deviations are calculated, and standard error of the means (error bars) are calculated for each condition (see FIG. 1).

Experimental conditions reveal fluorescently-labeled, antibody-targeted, lipid-enveloped cages bind to mCD22Ig significantly more than fluorescently-labeled, lipid enveloped non-targeted cages.

Anti-CD22 HSPC cages bound 1.6 times better than HSPC cages only, indicating that delivery systems are targeted with antibodies (FIG. 1).

Example 8

Figure 2:
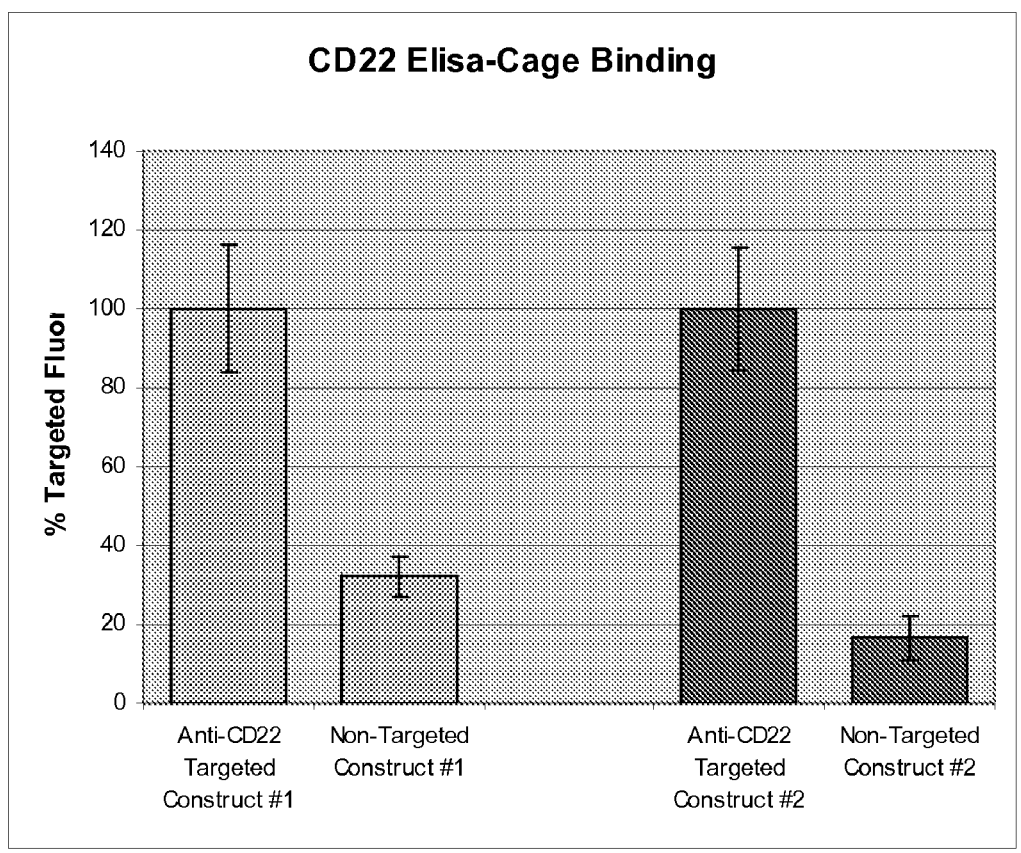
FIG. 2 is a bar chart showing that two identical nanocage preparations demonstrate consistent results when comparing the binding to mCD22Ig of anti-CD22 targeted nanocages over that of non-targeted nanocages. Anti-core protein antibodies were used to detect the presence of nanocages. Non-targeted nanocage binding data are normalized to the % of anti-CD22 targeted nanocage binding.

Evaluation of Target Specificity Cage Binding ELISA 96-well ELISA plates are coated with either 50 µL of mCD22Ig protein or 2% BSA (w/v) in 0.1M borate buffered saline at a concentration of 50 µg/mL overnight. Plates are then washed three times in Tris buffered saline (TBS). All wells are then blocked with 2% BSA in TBS for 1 hour, followed by three TBS rinses. Anti-CD22 targeted cage constructs and non-targeted cage constructs are incubated in triplicate, at multiple concentrations, in buffer containing 2% BSA and 0.1% Tween in TBS for four hours. Wells are then rinsed three times in TBS followed by incubation in antibodies generated against 1) rabbit-anti HBV core protein (AbCam), 2) mouse anti-HBV core protein (GenTex), or 3) no antibody in 2% BSA and 0.1% Tween in TBS for 1 hour. Wells are then rinsed three times in TBS followed by one hour incubation in 1) goat anti-rabbit IgG conjugated to alkaline phosphatase, 2) goat anti-mouse Fc region conjugated to alkaline phosphatase, or 3) no antibodies in 2% BSA and 0.1% Tween in TBS. All wells are rinsed three times in TBS, one time in PBS, and incubated in DDAO-phosphate (1:100,000) in PBS. Primary antibodies (rabbit-anti HBV core protein (AbCam) or mouse anti-HBV core protein (GenTex)) are omitted in background control wells. Fluorescent reads are conducted using Cy5 excitation/emission settings on a Typhoon Molecular Imager, and averaged; standard deviations are calculated, and standard error of the means (error bars) calculated for each condition (2 experiments included representing 2 cage preparations; see FIG. 2).

Separate ELISAs were also conducted to measure the amount of mouse anti-CD22 antibody is present on targeted cages versus non-targeted cages in each well (see above) using the same protocol but omitting the primary antibody step (rabbit-anti HBV core protein (AbCam) or mouse anti-HBV core protein (GenTex)). For these experiments, only goat anti-mouse Fc region specific antibodies were used to detect the presence of cages. DDAO-phosphate was used as the fluorescent substrate (see above) and all analyses were conducted in the same manner (see FIG. 3).

Figure 3:
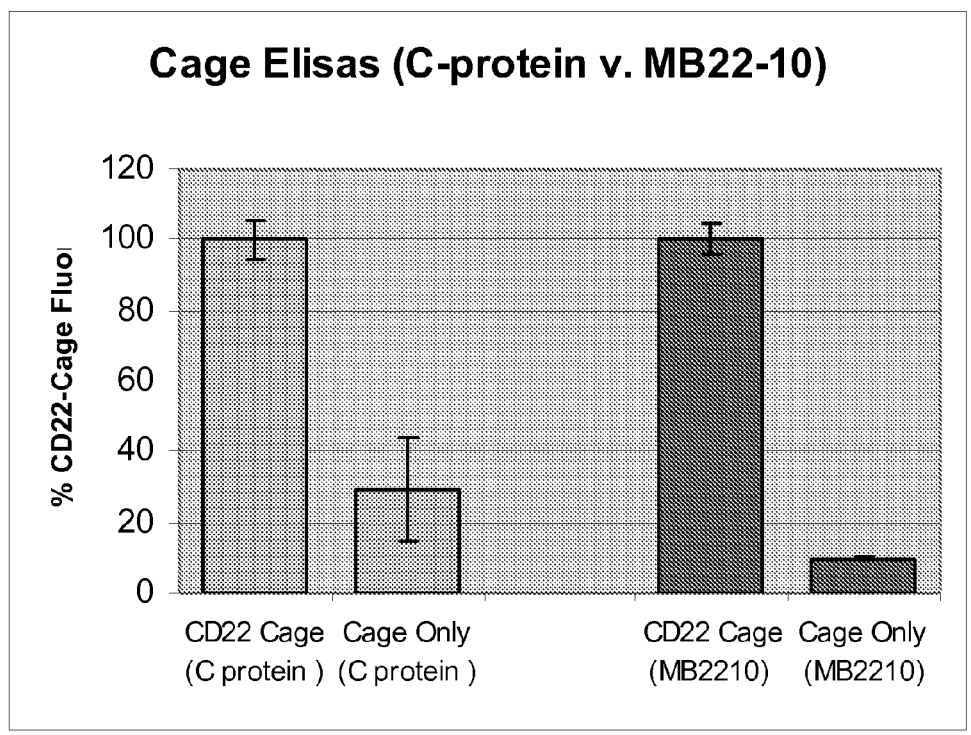
FIG. 3 is a bar chart showing two identical ELISA experiments conducted on the same nanocage preparation to demonstrate significantly more anti-CD22 targeted nanocage binding to mCD22Ig than non-targeted nanocages. Anti-core protein antibodies (light shaded columns on the left) and goat-anti-mouse antibodies (dark shaded columns on the right) were used to detect the presence of nanocages or anti-CD22 antibody on the surface of nanocages (respectively). Non-targeted nanocage binding data are normalized to the % of anti-CD22 targeted nanocage binding.

In the core protein assay it was found that delivery system bound 3.5 times better than non targeted system, indicating binding of antibodies to the delivery system surface. In the mCD22Ig binding studies anti-CD22 HSPC cages bound 9 times better than non targeted cages only, again indicating that delivery systems targeted with antibodies are more specific for a specific receptor (FIG. 3).

Example 9

Figure 4:
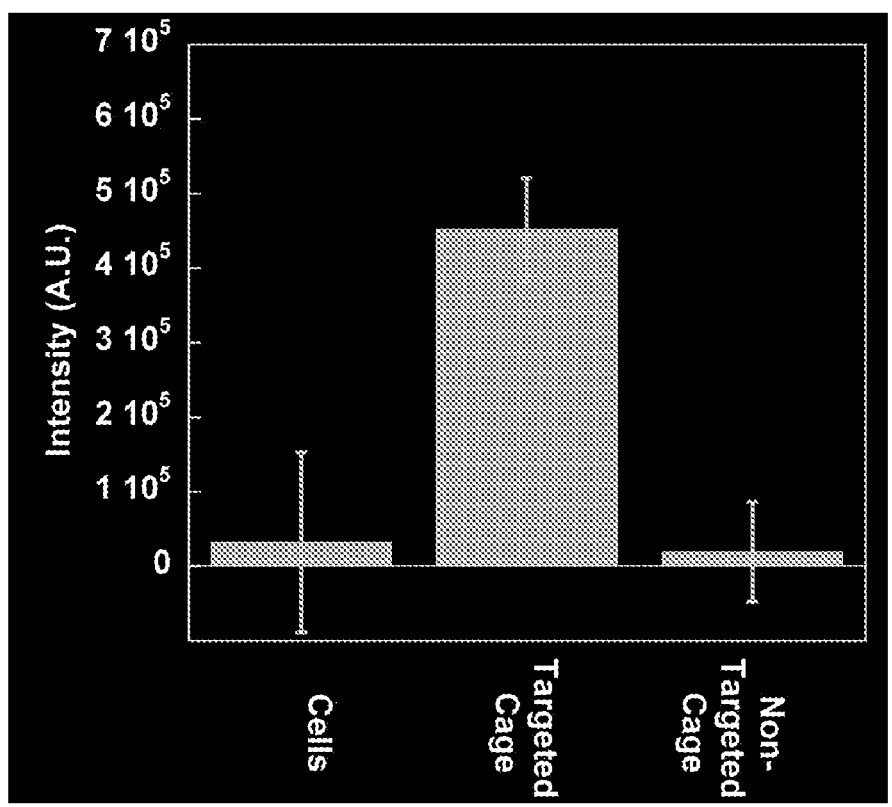
FIG. 4 is a bar chart showing that anti-CD22 targeted nanocages bind to B Cells (Ramos cells) significantly better than non-targeted nanocages. Background fluorescence of "cells alone" is included for comparison.

Evaluation of Anti-CD22 Targeted VS. Non-Targeted Fluorescent Cage Binding to Cells 9 mL Ramos cells (from cultures at a density of 1,000,000 cells/mL) are drawn from T75 culture flasks into 3 sterile 15 mL conical tubes (3 mL each), spun down, and resuspended in 3 mL complete RPMI medium (each). Cells are incubated with fluorescent anti-CD22 targeted cages, non-targeted cages (both with 3% DiI embedded in the lipid envelope), or an equal volume of "media only" at 37° C. at a concentration of 400,000 cages/cell in 3 mL (equal to ~60 nM) for 2 hours. Cells are then spun down, rinsed two times in 5 mL complete media, rinsed three times in 5 mL sterile PBS, spun down and resuspended in 150 µL of PBS. 150 µL of 2% paraformaldehyde is then slowly added to the cells. Cells are allowed to fix for 10 minutes, and 100 µL of cell suspension is added to each of 3 wells of a 96-well plate. Plates are then spun down using a clinical centrifuge and fluorescence is read on a Typhoon Molecular Imager using Cy3 excitation/emission settings. Fluorescent levels are averaged, standard deviations are calculated, and standard errors of the means (error bars) are calculated for each condition (see FIG. 4).

These results show that the targeted delivery systems get taken up by cells three times better than non targeted cages, indicating that targeting with antibodies for CD22 improves cellular uptake of the delivery system by B cells.

Example 10

Evaluation of Anti-CD22 Targeted VS. Non-Targeted Fluorescent Cage Binding Internalization Adherent BCL1 cells are plated onto glass coverslips (Fisher Scientific) in sterile 24-well tissue culture plates 12 hours prior to initiating the experiment. Cells are allowed to grow to semi-confluency (cell density estimated at 200,000 cells/well) in complete RPMI media (see Cell Growth above). To initiate the experiment, cells are rinsed once with media and 500 µL of media is then added to each well. Following experimental incubations (see below), adherent cells are rinsed once in media and three times in PBS. Cells are then resuspended in 150 µL PBS and 150 µL of 2% paraformaldehyde is added to tubes to slowly fix cells.

A total of 200,000 suspension cells (Ramos, Jurkat, or HH Cells) are added to sterile 24-well tissue culture plates and media and volumes are adjusted upwards to 500 μL with complete media. Following experimental incubations (see below), suspension cells are sequentially pelleted and rinsed once in media and three times in PBS. Cells are then resuspended in 150 μL PBS and 150 μL of 2% paraformaldehyde is added to tubes to slowly fix cells.

Figure 5:
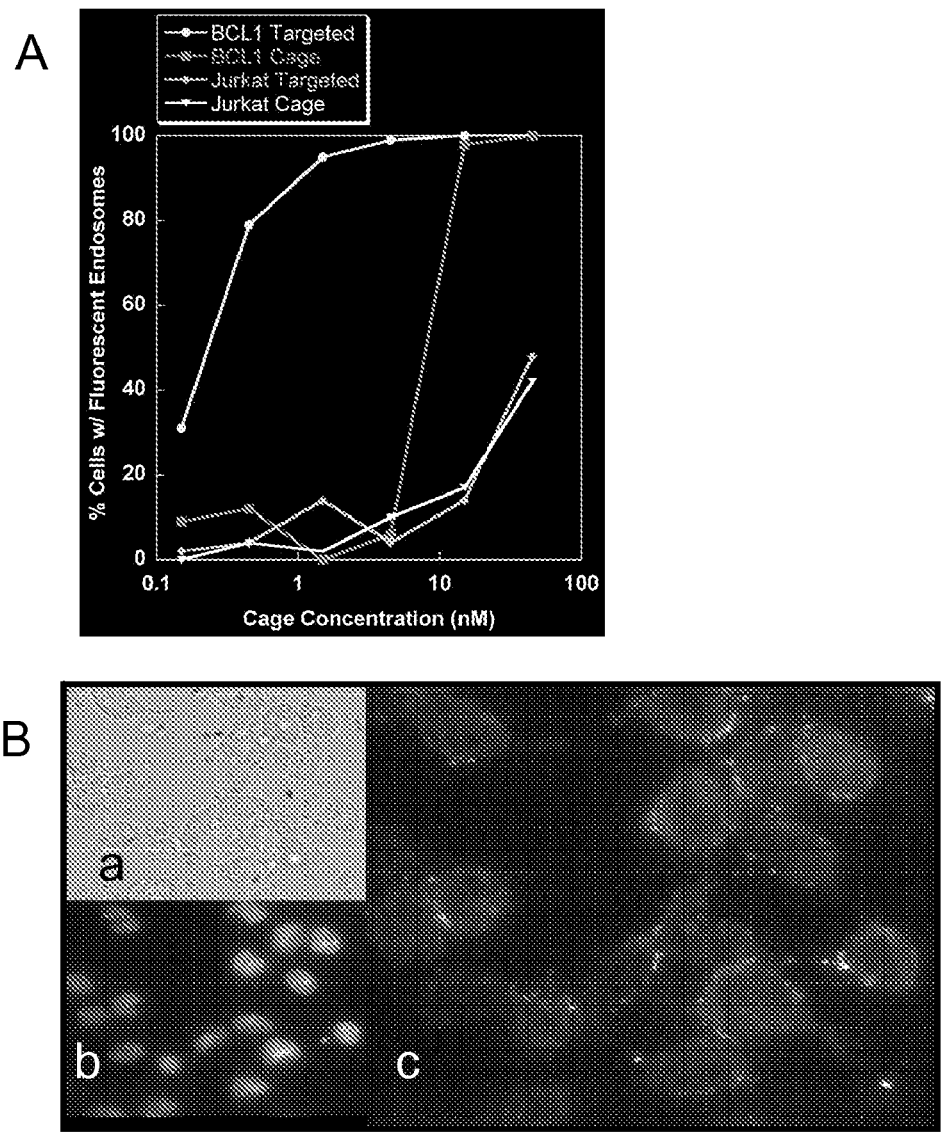
FIG. 5A is a line graph showing that anti-CD22 targeted nanocages bind to B cells (BCL1) with more specificity than they bind to T Cells (Jurkat). Non-targeted nanocages (nanocage) bind to both cell types with similar affinity at low concentrations, but better to B Cells at higher concentrations.
FIG. 5B is a photograph of semi-confluent BCL1 cells (a; brightfield), were counter stained with Hoechst 33342 (b) to reveal nuclei. Internalized nanocages are seen within all cells in the filed of view (c; 3 nM).
Figure 6:
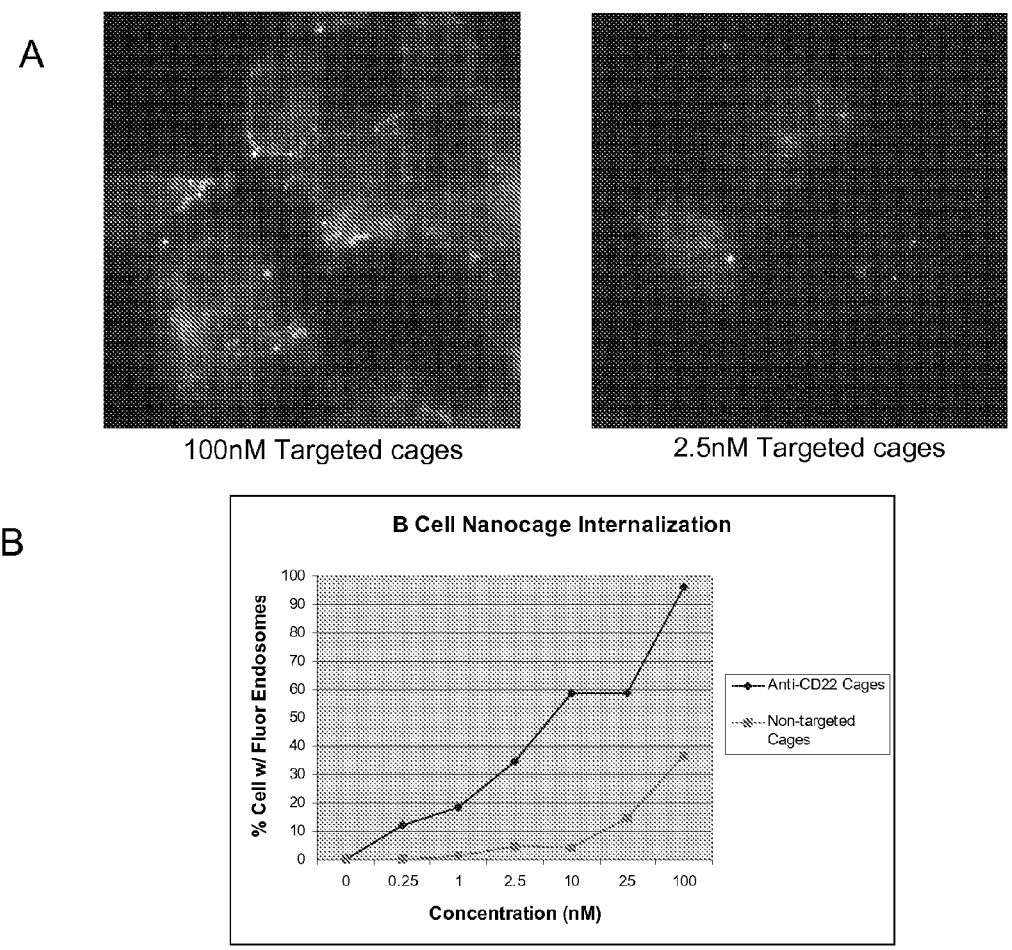
FIG. 6A are photographs showing internalized fluorescent nanocages are visible at 100 nM and 2.5 nM concentrations of anti-CD22 targeted nanocages.
FIG. 6B is a line graph showing the dose-response of anti-CD22 targeted nanocages and non-targeted nanocages in BCL1 cells.

For experimental incubations, cells (adherent and suspension) are incubated with fluorescent anti-CD22 targeted cages, non-targeted cages (both with 3% DiI embedded in the lipid envelope), or an equal volume of "media only" at 37° C. at multiple cage concentrations [300,000 cages/cell (~30 nM), 100,000 cages/cell (~10 nM), 30,000 cages/cell (~3 nM), 10,000 cages/cell (~1 nM), 3000 cages/cell (~300 μM), and 1000 cages/cell (~100 μM)] in 500 μL media for 2 hours. Following rinses and fixation (see above), cells are cover-slipped wet in 5% n-propyl gallate in glycerol (w/v) and sealed under coverslips using nail polish. Internalized fluorescent delivery systems are quantified using standard fluorescence microscopy. Two hundred cells are counted per coverslip and the percentage of cells with internalized cages is quantified (see FIGS. 5 and 6).

The results in FIG. 5A show that targeted delivery systems are preferentially internalized compared to non targeted delivery systems. Further, the targeted delivery system is specific for B-cells only when compared to similar dosage concentration used in T cell experiments. Targeting of the delivery system significantly improves targeted cell uptake when compared to non-specific cells.

The results in FIG. 6B show that targeted delivery systems are preferentially internalized compared to non targeted delivery systems.

Example 11

Competition Assay Using Anti-CD22 Targeted Cages in the Presence of "Free-Anti-CD22"

Figure 7:
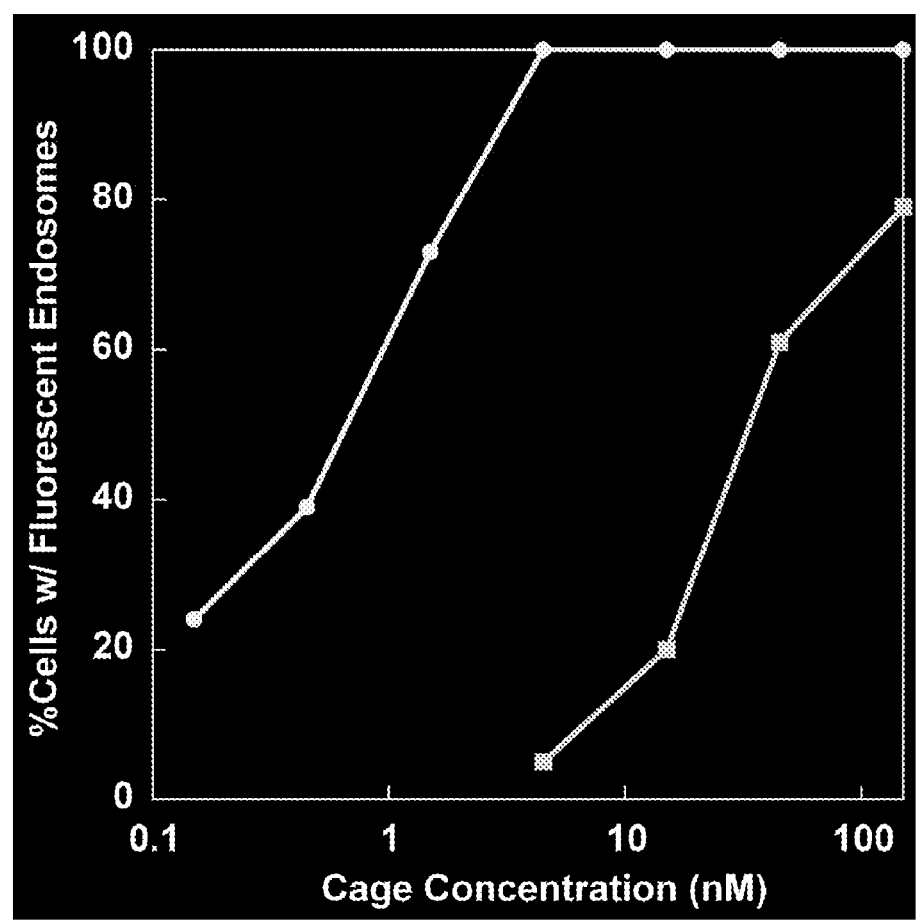
FIG. 7 is a line graph showing that "free" anti-CD22 antibody mixed with purified anti-CD22 targeted nanocages results in a >100-fold shift in the dose-response relationship of nanocage internalization in B Cells. Free anti-CD22 antibody containing preparations (squares); purified anti-CD22 targeted nanocages (circles).

Cage constructs were generated using standard procedures (see previous sections on cage production). Following antibody attachment to the delivery system, normal purification of cages away from free antibody using column chromatography was NOT conducted, resulting in the presence of free antibody (>10:1) in targeted cage preparations. Fluorescent internalization experiments were conducted using BCL1 cells and identical experimental conditions as stated above. Experimental incubations for this experiment included the comparison between identical concentrations of targeted cage (purified) and targeted cage (non-purified). Cage concentrations for all experiments are determined by quantifying core protein concentration, so free antibody did not effect concentration calculations. Analysis of internalized delivery system in these experiments was identical to those mentioned above (see FIG. 7).

These results further indicate that targeted cages are being internalized through surface marker-mediated internalization processes and are not internalized from the local environment through nonspecific endocytic pathways.

Example 12

Evaluation of Anti-CD22 Targeted Nanocages Loaded with Doxorubicin to Targeted and Kill CD22 Expressing Cells B cells (Ramos), and T cells (Jurkat) are added to wells of sterile 96-well plates (500,000 cells/ml) in early log growth phase. Complete growth media (see above) is added to each well after which both CD22-targeted nanocages and non-targeted nanocages loaded with doxorubicin are added across multiple concentrations of nanocage (10 pM, 100 pM, 1 nM, 10 nM, and 100 nM). Cells are assayed for viability using Tyrpan Blue exclusion at multiple time points (12 hr, 24 hr, 36 hr, 48 hr, 60 hr, and 72 hr). Cell viability is normalized to cell viability at the beginning of the experiments for each cell line and is expressed as a % of "normal". Cell density is also calculated and plotted across each time point for each concentration. All experiments at individual concentrations are conducted in triplicate for each time point.

Example 13

In Vivo Evaluation of Anti-CD22 Targeted Nanocages Loaded with Doxorubicin to Reduce Tumor Growth Female athymic BALB/c nu/nu mice (Harlan Sprague-Dawley), 7-9 weeks of age are maintained according to institutional animal care guidelines on a normal diet ad libitum and under pathogen-free conditions. Five mice are housed per cage. Raji or Ramos cells are harvested in logarithmic growth phase; $2.5\text{-}5.0 \times 10^6$ cells are injected subcutaneously into both sides of the abdomen of each mouse. Studies are initiated 3 weeks after implantation, when tumors are 100-300 mm$^3$. Groups consist of untreated, doxorubicin alone, naked nanocages loaded with doxorubicin, and nanocages loaded with doxorubicin and coated with HB22.7.

Tumor volume is calculated by the formula for hemiellipsoids (DeNardo G L, Kukis D L, Shen S, et al., Clin Cancer Res 1997; 3:71-79). Initial tumor volume is defined as the volume on the day prior to treatment. Mean tumor volume is calculated for each group on each day of measurement; tumors that have completely regressed are considered to have a volume of zero. Tumor responses are categorized as follows: C, cure (tumor disappeared and did not regrow by the end of the 84 day study); CR, complete regression (tumor disappeared for at least 7 days, but later regrew); PR, partial regression (tumor volume decreased by 50% or more for at least 7 days, then regrew).

Differences in response among treatment groups are evaluated using the Kruskall Walis rank sum test with the response ordered as none, PR, CR, and Cure. Survival time is also evaluated using the Kruskall Walis test. Tumor volume is compared at 3 time points: month 1 (day 26-29), month 2 (day 55-58), and at the end of the study (day 84). If an animal is sacrificed due to tumor-related causes, the last volume is carried forward and used in the analysis of later time points. Analysis of variance is used to test for differences among treatment groups. P values are two-tailed and represent the nominal p-values. Protection for multiple comparisons is provided by testing only within subsets of groups found to be statistically significantly different.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A targeted multi-layered drug delivery system comprising:
    a) a first layer comprising a nanocage made by self-assembly of a plurality of Hepatitis B Virus (HBV) core protein;
    b) a second layer comprising a lipid bi-layer made by self-assembly of a plurality of anionic or cationic lipids, wherein the lipid bi-layer is covalently attached to the nanocage;

c) a B-cell targeting moiety anchored into the lipid bi-layer; and d) at least one synthetic inhibitory RNA molecule encapsulated in the nanocage.

2. The drug delivery system of claim 1, wherein said B-cell targeting moiety is an anti-CD22 antibody, an anti-CD20 antibody, an anti-CD19 antibody, or an anti-FcR-H1 antibody.

3. The drug delivery system of claim 1, wherein said B-cell targeting moiety is a combination of antibodies specific for two or more of the B cell surface molecules selected from the group consisting of CD22, CD20, CD19, and FcR-H1.

4. The drug delivery system of claim 1, wherein said synthetic inhibitory RNA molecule is a dsRNA.

5. The drug delivery system of claim 4, wherein said dsRNA is a siRNA.

6. The drug delivery system of claim 1, wherein said synthetic inhibitory RNA molecule is an antisense RNA.

7. The drug delivery system of claim 1, wherein said HBV core protein comprises the amino acid sequence of SEQ ID NO: 1.

8. The drug delivery system of claim 7, wherein the glutamic acid at position 77 of SEQ ID NO: 1 is replaced with a cysteine.

9. The drug delivery system of claim 7, wherein the aspartic acid at position 78 of SEQ ID NO: 1 is replaced with a cysteine.

10. The drug delivery system of claim 7, wherein the alanine at position 80 of SEQ ID NO: 1 is replaced with a cysteine.

11. The drug delivery system of claim 1, wherein the lipid bi-layer comprises cholesterol.

12. The drug delivery system of claim 1, wherein the lipid bi-layer comprises phospholipids.

13. The drug delivery system of claim 12, wherein the phospholipids are selected from the group consisting of phosphatidyl ethanolamine, phosphatidyl glycerol and hydrogenated soy phosphatidyl choline (HSPC).

14. The drug delivery system of claim 1, wherein the lipid bi-layer comprises phosphatidyl glycerol, hydrogenated soy phosphatidyl choline (HSPC) and cholesterol.

15. The drug delivery system of claim 1, wherein the lipid bi-layer is covalently attached to the nanocage through a maleimide intermediate.

16. The drug delivery system of claim 8, wherein phosphatidyl-ethanolamine maleimide is attached to the cysteine at amino acid 77 of SEQ ID NO:1.

17. A targeted multi-layered drug delivery system comprising:
(a) a first layer comprising a nanocage comprising a plurality of modified Hepatitis B Virus (HBV) core protein;
(b) a second layer comprising a lipid bi-layer comprising a plurality of anionic or cationic lipids, wherein the lipid bi-layer is covalently attached to said first layer through a maleimide intermediate;
(c) a B-cell targeting moiety anchored to the lipid bi-layer; and
(d) at least one synthetic inhibitory RNA molecule encapsulated in the nanocage.

18. The self-assembling nanoparticle drug delivery system of claim 17, wherein the HBV core protein comprises SEQ ID NO: 1, wherein the glutamic acid at amino acid 77 is changed to a cysteine.

19. The drug delivery system of claim 17, wherein said B-cell targeting moiety is an anti-CD22 antibody, an anti-CD20 antibody, an anti-CD19 antibody, or an anti-FcR-H1 antibody.

20. The drug delivery system of claim 17, wherein said synthetic inhibitory RNA molecule is a dsRNA.

21. The drug delivery system of claim 17, wherein said dsRNA is a siRNA.

22. The drug delivery system of claim 17, wherein said synthetic inhibitory RNA molecule is an antisense RNA.

23. A targeted multi-layered drug delivery system comprising:
(a) a first layer comprising a nanocage comprising a plurality of modified Hepatitis B Virus (HBV) core protein comprising the amino acid sequence of SEQ ID NO: 1, wherein the glutamic acid at amino acid 77 is changed to a cysteine;
(b) a second layer comprising a lipid bi-layer comprising a plurality of anionic or cationic lipids, wherein the lipid bi-layer is covalently attached to said first layer by a phosphatidyl-ethanolamine maleimide to the cysteine at amino acid 77 of SEQ ID NO: 1;
(c) a B-cell targeting moiety anchored to the lipid bi-layer; and
(d) at least one synthetic inhibitory RNA molecule encapsulated in the nanocage.

24. The drug delivery system of claim 23, wherein said B-cell targeting moiety is an anti-CD22 antibody, an anti-CD20 antibody, an anti-CD19 antibody, or an anti-FcR-H1 antibody.

25. The drug delivery system of claim 23, wherein said synthetic inhibitory RNA molecule is a dsRNA.

26. The drug delivery system of claim 25, wherein said dsRNA is a siRNA.

27. The drug delivery system of claim 23, wherein said synthetic inhibitory RNA molecule is an antisense RNA.

28. A method for delivering a drug to a B-cell comprising contacting the cell with the drug delivery system any one of claim 1, 17 or 23.

\* \* \* \* \*